United States Patent [19]

Goodman et al.

[11] Patent Number: 5,298,272

[45] Date of Patent: Mar. 29, 1994

[54] BRIDGED CARBOXYLIC ORTHO ESTER SWEETENER

[75] Inventors: Murray Goodman, La Jolla, Calif.; Yeong S. Oh, Daejeon, Rep. of Korea

[73] Assignee: The Regents of the University of California, Oakland, Calif.

[21] Appl. No.: 984,879

[22] Filed: Dec. 2, 1992

[51] Int. Cl.$^5$ .................. A23L 1/236; C07D 319/14
[52] U.S. Cl. ........................... 426/548; 549/363
[58] Field of Search .................... 549/363; 426/548

[56] References Cited

PUBLICATIONS

Mazur, R. H., "Discovery of Aspartame," Food Sci. and Technol, 1984, 12, 3.

Mazur, R. H., Schlatter, J. M., Goldkamp, A. H., "Structure-Taste Relationships Of Some Dipeptides," J. Am. Chem. Soc., 1969, 91, 2684.

Grenby, T. H. (Ed.), Progress In Sweeteners, pp. 1–46, Elssevier Applied Science, London, New York.

Goodman, M., Coddington, J., Mierke, D. F., Fuller, W. D., "A Model For The Sweet Taste Of Stereoisomeric Retro-Inverso And Dipeptide Amides," J. Am. Chem. Soc. 1987, 109, 4712.

Goodman, M.; Miercke, D. F., Fuller, W. D., "A Stereoisomeric Approach To The Molecular Basis Of Taste Of Retro-Inverso And Dipeptide Amides," Proceedings Of The Japan Symposium On Peptide Chemistry, T. Shiba, S. Sakakibara (Eds.), Protein Research Foundation, Japan 1988, pp. 699–704.

Mazur, R. H., Reuter, J. A., Swiatek, K. A., And Schlatter, J. M., "Synthetic Sweetners.3. Aspartyl Dipeptide Esters From L- and D-Alkylglycines," J. Med. Chem., 1973, 16, 11.

Primary Examiner—Joseph Golian
Attorney, Agent, or Firm—Poms, Smith, Lande & Rose

[57] ABSTRACT

A sugar substitute which is identified as N-(L)-aspartyl-1-(1'-aminoethyl)-4-methyl-2,6,7-trioxabicyclo[2,2,2]octane. The compound is a bridged carboxylic ortho ester which has an intense sweet taste and is suitable for use as a sugar substitute.

10 Claims, No Drawings

BRIDGED CARBOXYLIC ORTHO ESTER SWEETENER

BACKGROUND OF THE INVENTION

1. Field of the Invention

The present invention relates generally to synthetic compounds which are useful as artificial sweeteners to be used in connection with beverages and foodstuffs designed for human consumption. More particularly, the present invention relates to the discovery of a new bridged carboxylic ortho ester which possesses an intense sweet taste and is suitable for use as an artificial sweetener.

2. Description of Related Art

Aspartame (L-aspartyl-L-phenylalanine methyl ester) is a well-known artificial sweetener which was accidentally discovered by James M. Schlatter in the 1960's (Mazur, R. H. *Food Sci. and Technol.*, 1984, 12, 3). Since its discovery, aspartame and a number of derivatives of this remarkable and potent sweetener have been subjected to many investigations. For example, Mazur et al. found that substitution of the aspartyl moiety leads to bitter or tasteless analogues (Mazur, R. H. Schlatter, J. M.; Goldkamp, A. H. *J. Am. Chem. Soc.*, 1969, 91, 2684). Other investigations involved replacing the phenylalanine methyl ester group with a wide variety of different amino acids providing either D-configurations with a small side chain and a large ester group or an L-configuration with a large side chain and a small ester group (See Grenby, T. H. (ed.), Progress in Sweeteners, Elssevier Applied Science, London, N.Y.).

In other studies, L-aspartyl-alanine 2,2,5,5,-tetramethylcyclopentyl amides and analogous retro-inverso derivatives have been investigated. For these compounds, it was observed that the L,L amide had a bitter taste while the L,D amide and the retro-inverso analogues had a sweet taste (Fuller, W. D.; Goodman, M.; Verlander, M. S. *J. Am. Chem. Soc.*, 1985, 107, 821).

A number of conformational studies have been undertaken to establish and explain the relationship between the structure and sweet taste of these compounds. For example, conformational studies using computer simulation, NMR and X-ray diffraction have been used to propose structural models for sweet tasting compounds (See Goodman, M.; Coddington, J.,; Mierke, D. F.; Fuller, W. D. *J. Am. Chem. Soc.* 1987, 109, 4712 and Goodman, M.; Miercke, D. F.; Fuller, W. D. in: Peptide Chemistry: Proceedings of the Japan Symposium on Peptide Chemistry, T. Shiba, S. Sakakibara (eds.), Protein Research Foundation, Japan 1988, pp. 699–704).

Even though aspartame and various dipeptide analogues have been studied extensively, it is still difficult to predict with any certainty the relationship between specific structures and their taste. For example, it has been observed repeatedly that small structural changes in various aspartame analogues can have dramatic effects on the taste of the compound. As a result, the discovery of new synthetic sweeteners is still unpredictable.

SUMMARY OF THE INVENTION

In accordance with the present invention, a new compound has been discovered which possesses a potent sweet taste. The synthetic sweetener in accordance with the present invention is a bridged carboxylic ortho ester which has the formula N-(L)-Aspartyl-1-(1'-aminoethyl)-4-methyl-2,6,7-trioxabicyclo[2,2,2]octane.

The compound in accordance with the present invention has a potent sweet taste which makes it particularly well-suited for use a substitute for sugar in beverages and foodstuffs. The new sweetener is an artificial compound which is stable and which is prepared utilizing known synthetic techniques.

As a feature of the present invention, the sweet taste intensity of N-(L)-Aspartyl-1-(1'-aminoethyl)-4-methyl-2,6,7-trioxabicyclo[2,2,2]octane is three to four times that of aspartame. Further, this compound in accordance with the present invention does not have any undesirable aftertaste. The intense sweetness of N-(L)-Aspartyl-1-(1'-aminoethyl)-4-methyl-2,6,7-trioxabicyclo[2,2,2]octane makes it possible adequately to sweeten beverages and foodstuffs by adding relatively small amounts of the sweetener.

The above-described and many other features and attendant advantages of the present invention will become apparent as the invention becomes better understood by reference to the following detailed description when considered in conjunction with the accompanying drawings.

DETAILED DESCRIPTION OF THE INVENTION

The synthetic sweetener in accordance with the present invention is a bridged carboxylic ortho ester which is identified as N-(L)-aspartyl-1-(1'-aminoethyl)-4-methyl-2,6,7-trioxabicyclo[2,2,2]octane. The compound may alternatively be represented by the following formula

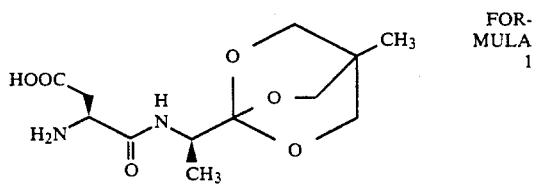

FORMULA 1

The compound of the present invention is an L-aspartyl-D-alanine ortho ester which is preferably prepared according to the following synthetic pathway.

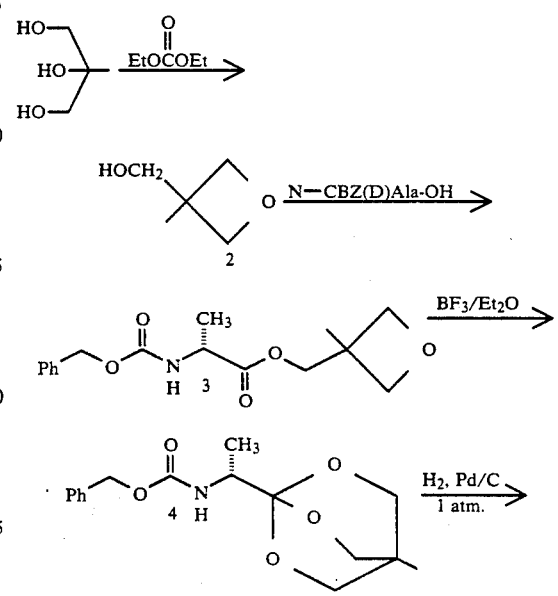

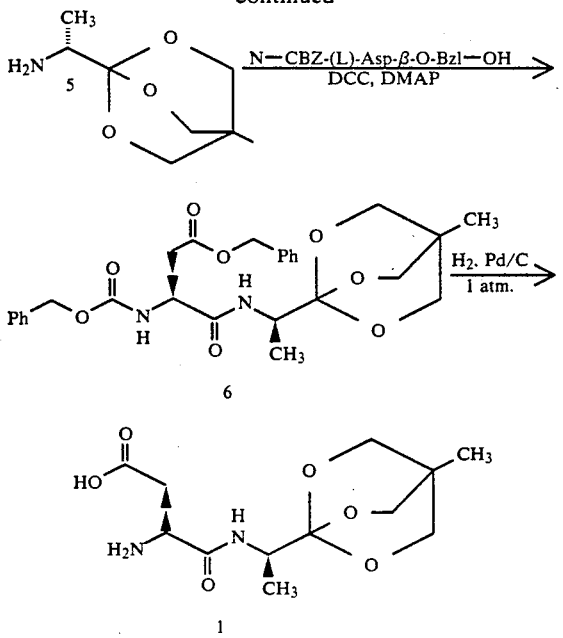

In the first step of the process, 1,1,1-tris(hydroxymethyl) ethane is treated with ethyl carbonate to produce the oxetane (2). This synthetic step is described in detail in (Corey, E. J.; Raju, N. *Tetrahedron Lett.*, 1983, 24, 5571. N-benzyloxycarbonyl-L-alanine is then esterified with the oxitàne (2) to form the oxitane ester (3). The oxitane ester (3) is then isomerized to the bridged ortho ester (4) utilizing $BF_3Et_2O$ in accordance with known isomerization procedures. See, for example, E. J. Corey and N. Raju, Tetrahedron Letters 24 5571–5574 (1983). The bridged ortho ester (4) is then deprotected to produce compound 5. The deprotection of the bridged ortho ester (4) is preferably accomplished utilizing hydrogen and a palladium/carbon catalyst in accordance with known techniques (See Peptide Synthesis, 2nd Ed., M. Bodansky, Y. S. Klausner and M. A. Ondretti, John Wiley and Sons, NY 1976). Compound 5 is then coupled to N-benzyloxycarbonyl-L-aspartic acid-β-benzyl ester by the carbodiimide reaction to produce compound 6. Compound 6 is then deprotected in the same manner that compound 4 was deprotected. Deprotection of compound 6 results in the formation of N-(L)-aspartyl-1-(1′-aminoethyl)-4-methyl-2,6,7-trioxabicyclo[2,2,2]octane (1).

Although other possible synthetic pathways are possible to produce the compound of the present invention (1), the above pathway is preferred since the above pathway utilizes known synthesis techniques which utilize starting compounds which are either commercially available or synthesized according to well-known procedures.

An exemplary synthesis of an N-(L)-aspartyl-1-(1′-aminoethyl)-4-methyl-2,6,7-trioxabicyclo[2,2,2]octane (1) is as follows.

The compound 3-Methyl-3-hydroxymethyloxetane (2) was prepared as follows. A mixture of 1,1,1-tris(hydroxymethyl)ethane 60 g, 0.5 mole), ethyl carbonate (59 g, 0.5 mole) and KOH (0.5 g in 2.5 ml of ethanol) was heated to reflux under nitrogen for 2 hours. After removal of ethanol at atmospheric pressure, fractional distillation under reduced pressure (20 mmHg) gave 43 g of yellow liquid. Redistillation of this crude product furnished 3-methyl-3-hydroxymethyloxetane (2) as a colorless oil: yield 38 g (74.5%); $^1H$ NMR ($CDCl_3$) δ 1.29 (s, 3H, $CH_3$), 2.77 (br s, 1H, OH), 3.68 (s, 2H, $CH_2$,OH), 4.40 and 4.54 (2d, 4H, $(CH_2)_2O$) ppm.

The 3-methyl-3-hydroxymethyloxetane ester of N-benzyloxycarbonyl-(D)-alanine (3) was prepared as follows. A solution of compound 2 (0.92 g, 9.02 mmole) and N-benzyloxycarbonyl-(D)-alanine (2.0 g, 9.02 mmole) in dichloromethane (20 ml), 1,3-dicyclohexylcarbodiimide (DCC, 1.86 g, 9.02 mmol) and 4-dimethylaminopyridine (DMAP, 55 mg, 0.45 mmole), were added at 0° C. The reaction mixture was vigorously stirred at room temperature for 3 hours. The undissolved solid was filtered through a Celite bed and the filtrate was concentrated under reduced pressure. The residue was purified by flash column chromatography over silica gel (pretreated with 1% triethylamine in hexane) using 40% ethyl acetate-hexane as the eluent to give compound 3: yield 2.1 g (76%); $R_f$ 0.33 (40% ethyl acetate-hexane); $^1H$ NMR (DMSO-$d_6$) δ 1.23 (s, 3H, $CCH_3$, 1.38 (d, J=7.1 Hz, 3H, $CHCH_3$), 4.16–4.37 (m, 7H, $(CH_2)_3C$ and $CHCH_3$), 5.0 (s, 2H, $CH_2C_6H_5$), 7.37 (m, 5H, $C_6H_5$), 7.79 (d, J=7.5 Hz, 1H, NH) ppm.

The 1-(1′-(N-benzyloxycarbonyl)aminoethyl)-4-methyl-2,6,7-trioxabicyclo[2,2,2]octane (4) was prepared as follows. To a solution of oxetane ester (3) (2 g, 6.5 mmole) in dichloromethane (10 ml) at −15° C., distilled boron trifluoride etherate (0.2 ml, 1.62 mmole) was added. The reaction mixture was further stirred at −15° C. (12h) and quenched by addition by triethylamine (0.9 ml, 6.5 mmole). The solvent was removed under reduced pressure and the crude product was purified by flash column chromatography over silica gel (pretreated with 1% triethylamine in hexane) using 40% ethyl acetate-hexane as the eluent to give 1-(1-(N-benzyloxycarbonyl)aminoethyl)-4-methyl-2,6,7-trioxabicyclo[2,2,2]octane (4): yield 1.7 g (85%); $R_f$ 0.40 (40% ethyl acetate-hexane); $^1H$ NMR (DMSO-$d_6$) δ 0.76 (s, 3H, $CCH_3$), 1.12 (d, J=7.1 HZ, 3H, $CHCH_3$), 3.82 (s, 6H, $(CH_2)_3C$), 5.01 (s, 2H, $CH_2C_6H_5$), 6.92 (d, J=7.5 Hz, 1H, NH), 7.36 (m, 5H, $C_6H_5$)ppm.

The 1-(1′-aminoethyl)-4-methyl-2,6,7-trioxabicyclo[2,2,2]octane (5) was prepared as follows. To a solution of ortho ester 4 (1.5 g, 4.89 mmol) in methanol (20 ml), catalytic amount of 10% palladium on activated carbon (50 mg) was added. The reaction mixture was stirred under hydrogen at atmospheric pressure for 6 hours. The catalyst was filtered through a Celite bed and the solvent was removed under reduced pressure to produce compound 5: yield 820 mg (97%); $^1H$ NMR ($CDCl_3$) δ 0.81 (S, 3H, $CCHD_3$), 1.11 (d, J=7.2 Hz, 3H, $CHCH_3$), 1.77 (s, 2H, $NH_2$), 2.92 (q, J=7.2 Hz, 1H, $CHCH_3$), 3.90 (s, 6H, $(CH_2)_3C$) ppm.

Synthesis of N-benzyloxycarbonyl-(L)-aspartyl-δ-benzyl ester-1-(1′-aminoethyl)-4-methyl-2,6,7-trioxabicyclo[2,2,2]octane (6) was accomplished as follows. To a solution of compound 5 (750 mg, 4.34 mmole) in dichlorormethane (20 ml), 1,3-dicyclohexylcarbodiimide (900 mg, 4.34 mmole) and 4-dimethylaminopyridine (27 mg, 0.22 mmole) were added at 0° C. The reaction mixture was vigorously stirred at room temperature for 3 hours. The undissolved solid was filtered through a Celite bed and the filtrate was concentrated under reduced pressure. The residue was purified by flash column chromatography over silica gel (pretreated with 1% triethylamine in hexane) using 40% ethyl acetate-hexane as the eluent to furnish the pure compound 6: yield 1.9.3 g (87%); $R_f$ 0.16 (40% ethyl acetate-hexane); $^1$H NMR (DMSO-$d_6$) δ 0.76 (s, 3H, CCH$_3$), 0.97 (d, J=7.0 Hz, 3H, CHCH$_3$), 2.60 and 2.76 (2m, 2H, CHCH$_2$), 3.83 (m, 1H, CHCH$_3$):, 4.44 (m, 1H, CHCH$_2$), 5.03 and 5.05 (2s, 4H, 2 X CH$_2$C$_6$H$_5$), 7.37 (m, 10H, 2X C$_6$H$_5$). 7.46 and 7.61 (2d, J=7.5 Hz, 2H, 2 X NH) ppm.

Final preparation of N-(L)-aspartyl-1-(1'-aminoethyl-4-methyl-2,6,7-trioxabicyclo[2,2,2]octane (1) was carried out as follows. To a solution of compound 6 (1.8 g, 3.51 mmole) in methanol (20 ml), catalytic amount of 10% palladium on activated carbon (50 mg) was added. The reaction mixture was stirred at room temperature under hydrogen at atmospheric pressure for 5 hours. The catalyst was filtered through a Celite bed and the sweetener (1) was recrystallized from the boiling methanol: yield 810 mg (80%); $^1$H NMR (DMSO-$d_6$) δ 0.78 (s, 3H, CCH$_3$), 1.02 (d, J=7.0 Hz, 3H, CHCH$_3$), 2.11 and 2.40 (2m, 2H, CHCH$_2$), 3.62 (m, CHCH$_2$), 3.83 (s, 6H, (CH$_2$)$_3$C), 3.88 (m, 1H, CHCH$_3$), 8.16 (d, J=7.5 Hz, NHC(O))ppm.

The sweetener (1) in accordance with the present invention is in the form of clear crystals at room temperature which are readily dissolved in water or alcohol. The sweetener 1 may be added to foodstuffs either before or after processing in the same manner as sugar is added. For most purposes, the sweetener (1) can be substituted directly for sugar, except that much smaller amounts of sweetener (1) can be used because of the intense sweetness of the compound.

The sweetener may be added to solid foodstuffs including baked goods and may be used in a variety of food recipes wherein sugar or other sweetener is required. Also, the compound of the present invention may be added in varying amounts to liquids as a sugar substitute. The amount of sweetener (1) which is added to the foodstuff or beverage may be varied widely depending upon the desired degree of sweetness. In general, the weight % of sweetener (1) present in most food and beverages will be on the order of between about 0.01 and 5%. The intense sweetness of the compound (1) in accordance with the present invention must be taken into account when adding it to various foodstuffs and beverages since even small amounts of the sweetener present in the food or beverage will impart an intense sweet taste. On a weight basis, compound 1 is about 500 times sweeter than sucrose and has about the same sweetness as sodium saccharin.

The sweetener of the present invention is suitable for use as a substitute for sucrose, sodium saccharin or aspartame and can be used in all of the same types of foods and beverages to which sucrose, sodium saccharin and aspartame are added. In addition, the sweetener of the present invention may be utilized in pure form for direct addition to foods and beverages prior to consumption. Since the compound of the present invention is a solid crystalline material at room temperature, it is particularly well-suited for packaging into a variety of package sizes for use in a wide variety of situations including use as a bulk additive in large scale production of foodstuffs. The sweetener is equally well-suited for packaging in small containers for use by individuals as a sugar substitute to be added to individual servings of food to achieve desired sweetness.

The sweetener (1) of the present invention is a 4-methyl-2,6,7-trioxabicyclo[2,2,2]octane ortho ester derived from (L)-aspartyl-(D)-alanine. The (L)-aspartyl-(L)-alanine analog of sweetener (1) was prepared following the exemplary set forth above except that N-benzloxy carbonyl-(L)-alanine was used in place of N-benzloxycarbonyl-(D-alanine. The results (L)-aspartyl-(L)-alanine ortho ester was found to have a bitter taste.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A composition of matter comprising a compound identified as N-(L)-aspartyl-1-(1'-aminoethyl)-4-methyl-2,6,7-trioxabicyclo[2,2,2]octane.

2. A composition of matter consisting essentially of the compound identified as N-(L)-aspartyl-1-(1'-aminoethyl)-4-methyl-2,6,7-trioxabicyclo[2,2,2]octane.

3. A composition of matter which comprises a sufficient amount of a compound identified as N-(L)-aspartyl-1-(1'-aminoethyl)-4-methyl-2,6,7-trioxabicyclo[2,2,2]octane to impart a sweet taste to said composition of matter.

4. A composition of matter according to claim 3 wherein the weight percent of said compound present in said composition of matter is between about 0.01% and 5%.

5. A composition of matter according to claim 3 wherein said composition of matter is a liquid.

6. A composition of matter according to claim 5 wherein said liquid is a beverage.

7. A composition of matter according to claim 3 wherein said composition of matter is a solid.

8. A composition of matter according to claim 7 wherein said solid is a foodstuff.

9. A method for imparting a sweet taste to a composition of matter comprising adding a sufficient amount of a compound identified as N-(L)-aspartyl-1-(1'-aminoethyl)-4-methyl-2,6,7-trioxabicyclo[2,2,2]octane to said composition of matter to impart a sweet taste thereto.

10. A method for imparting a sweet taste to a composition of matter according to claim 9 wherein a sufficient amount of said compound is added to said composition of matter so that the weight percent of said compound in said composition of matter is between about 0.01% and 5%.

* * * * *